United States Patent [19]

van Driessche

[11] Patent Number: 4,995,967
[45] Date of Patent: Feb. 26, 1991

[54] SEPARATOR FOR CELL-CONTAINING LIQUIDS

[75] Inventor: Petrus J. D. M. van Driessche, St. Jansteen, Netherlands

[73] Assignee: Akzo N.V., Netherlands

[21] Appl. No.: 261,326

[22] Filed: Oct. 24, 1988

[30] Foreign Application Priority Data

Nov. 6, 1987 [NL] Netherlands .................... 8702652

[51] Int. Cl.$^5$ ............................................. B01D 69/08
[52] U.S. Cl. ........................................ 210/94; 210/188; 210/321.88; 210/321.89; 210/433.1; 210/456; 210/500.23; 435/292; 435/299; 435/311; 422/58; 422/101; 422/102
[58] Field of Search ................ 210/321.78, 321.79, 210/321.8, 321.81, 321.87, 321.88, 321.89, 321.9, 500.23, 94, 188, 433.1, 456; 422/58, 101, 73, 102; 435/292, 296, 311, 299

[56] References Cited

U.S. PATENT DOCUMENTS

| 3,608,730 | 9/1971 | Blahs | 210/321 |
| 3,774,771 | 11/1973 | Manjikian et al. | 210/321 |
| 4,267,053 | 5/1981 | Hashino et al. | 210/321.87 |
| 4,412,916 | 11/1983 | Kell | 210/188 |
| 4,628,036 | 12/1986 | Sheepens et al. | 422/102 |
| 4,639,316 | 1/1987 | Eldegheidy | 210/416.1 |
| 4,668,401 | 5/1987 | Okumura et al. | 210/321.87 |
| 4,690,754 | 9/1987 | Koyama et al. | 210/94 |

OTHER PUBLICATIONS

English Abstract of Japanese Application 60-54710.
English Abstract of Japanese Application 60-247163.

Primary Examiner—W. Gary Jones
Assistant Examiner—Matthew O. Savage
Attorney, Agent, or Firm—Oliff & Berridge

[57] ABSTRACT

A device for separating a cell-containing liquid into a cell-containing and a cell-free fraction, which device comprises an essentially elongated housing at one end of which there is provided a closable inlet, which housing contains an area for the cell-containing fraction, an area for the cell-free fraction and a membrane separator, which separator comprises a narrow feed channel through which the cell-containing liquid is passed over the wall of a separation membrane, which is formed by one or more hollow fibres which are connected at their open ends to the area for the cell-free fraction.

Thus, for example, whole blood is separated very rapidly after its introduction into the device. The device may be manufactured simply and inexpensively and is pre-eminently suitable to be used for diagnostic purposes.

5 Claims, 4 Drawing Sheets

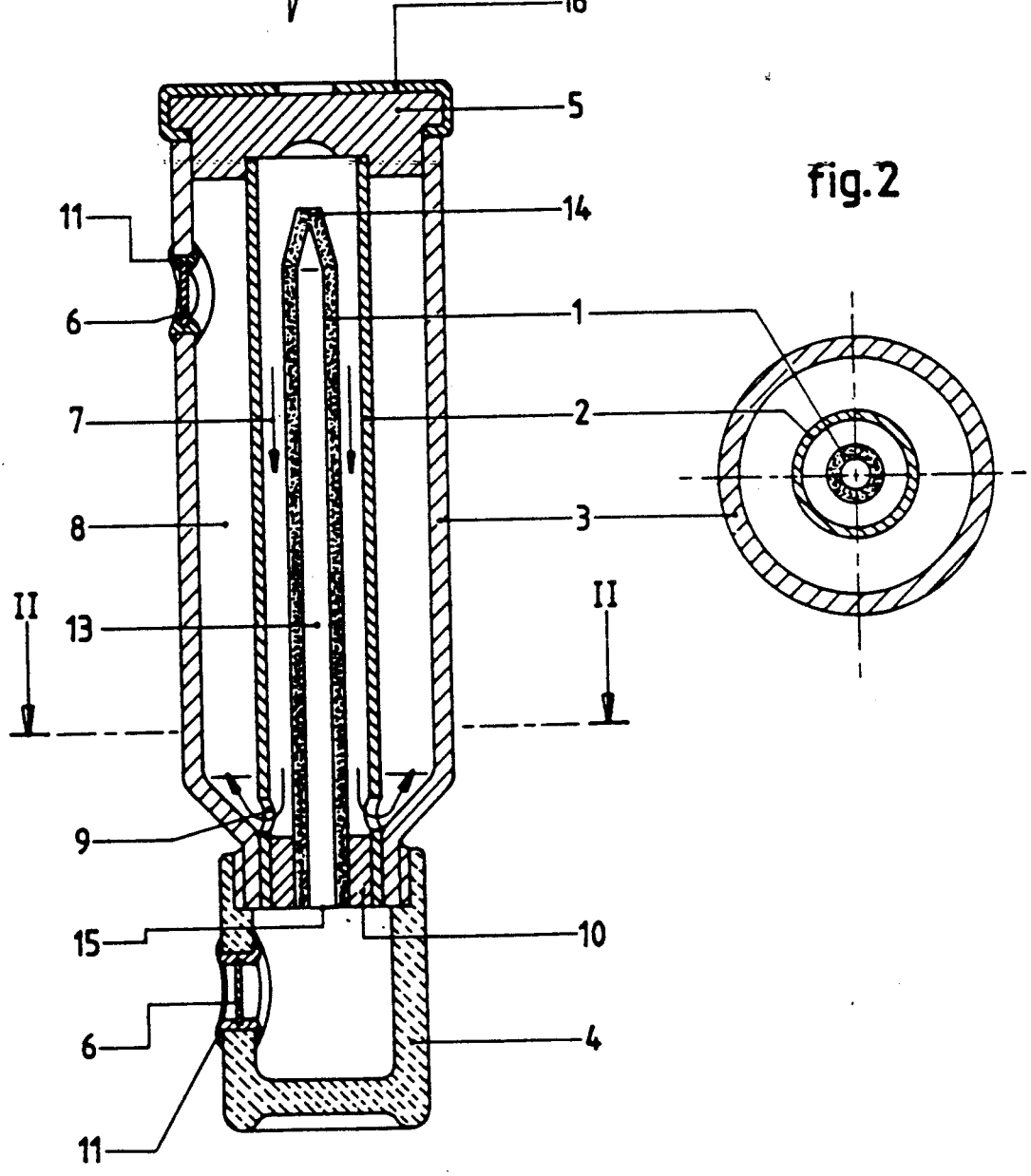

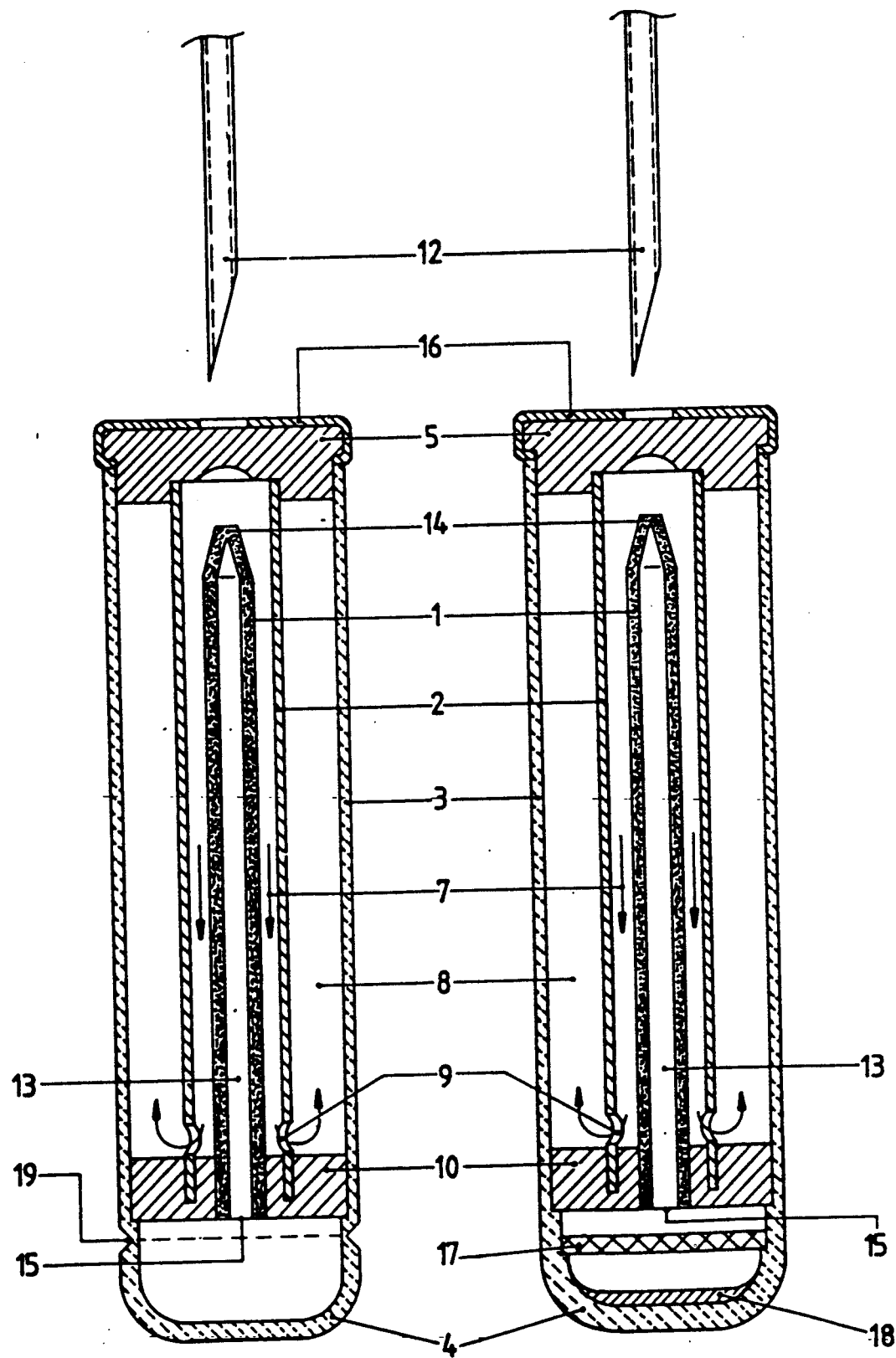

SEPARATOR FOR CELL-CONTAINING LIQUIDS

The invention relates to a device for separating a cell-containing liquid into a cell-containing and a cell-free fraction, which device comprises an essentially elongated housing at one end of which there is provided a closable inlet, which housing contains an area for the cell-containing fraction, an area for the cell-free fraction, and a membrane separator, which separator comprises a narrow feed channel through which the cell-containing liquid is passed over the wall of a separation membrane. An apparatus of the type indicated above has been proposed before in European Patent Application 184,852.

In the device described therein the membrane separator comprises a space containing a flat membrane which is attached to a grid and which membrane is positioned between two walls spaced slightly therefrom.

From the upper end of the separator the cell-containing liquid is passed down over the membrane and at the lower end it is discharged as cell-containing fraction to an area for collecting this fraction. Through channels on the other side of the membrane the cell-free fraction is passed to an area for collecting that fraction. In the closable inlet there are various provisions for a uniform distribution of the cell-containing liquid across the entire width of the membrane.

Although the separating devices described therein permit obtaining a cellfree fraction (plasma) in an amount sufficiently high for diagnostic purposes, in view of the single use of these devices in medical practice there is a great need for separating devices of a simpler and less expensive construction.

The present invention provides a device which largely meets said need. The invention comprises an apparatus of the known type mentioned in the opening paragraph wherein the membrane is formed by one or more hollow fibres which are connected at their open ends to the area for the cell-free fraction.

It should be added that separators for cell-containing liquids comprising membranes composed of one or more hollow fibres are known in themselves. GB-A-2,173,711, for example, describes a separator for blood, for instance, in which the driving force needed to bring about filtration is obtained either by a difference in pressure created between the outside and the inside of the hollow fibre or by the use of a centrifugal force.

In Patent Abstracts of Japan, Vol. 9, No 184 (C-294)(1907) July 30, 1985 also mention is made of a hollow fibre membrane. In that case, however, the liquid to be filtered is passed through a thin tube inside the lumen of a hollow fibre. Unlike the device according to the invention, this known filter is a dead-end filter as is the one according to GB-A 2173711.

In Patent Abstracts of Japan, Vol. 10, No. 119 (P-453)(2176), May 6, 1986 mention is made of a separator comprising a bundle of hollow fibres. In this device, too, the blood to be filtered is passed through the hollow fibres. In the separators according to the present invention, however, the cell-containing liquid is passed over the outside of the hollow fibre(s). The use of one or more hollow fibres in a narrow feed channel results in a far simpler construction permitting a proper contact between the cellcontaining liquid and the separation membrane.

For a proper functioning of the separating device according to the invention it is of importance that the cell-containing liquid should pass along the wall of the hollow fibres at a sufficiently high shear rate. The attendant shear stress acting as driving force will then bring about the desired filtration.

In this connection the distance between the wall of the feed channel and that of the hollow fibres will generally be in the range of 20 to 200 $\mu$m. A distance smaller than 20 $\mu$m will readily give rise to hemolysis and possibly to long filtration times, and at a distance greater than 200 $\mu$m the shear rate will generally be too low, resulting in a low plasma yield. According to the invention it is preferred that in the separating device the distance between the wall of the feed channel and that of the hollow fibres should be in the range of 50 to 100 $\mu$m.

As hollow fibres suitable for use according to the invention may be employed such fibres as are also used in dialysis, ultrafiltration and plasmapheresis. They generally have an inner diameter of 250-750 $\mu$m, preferably 300-400 $\mu$m, and their wall thickness is usually in the range of 100 to 300 $\mu$m. Their outer diameter generally ranges from 0.2 to 1.5 mm. The individual pores in the membrane generally measure from 0.1 to 1.2 $\mu$m and are preferably about 0.45 $\mu$m.

The material from which the hollow fibres are made should be hydrophilic. As examples of suitable fibre materials may be mentioned polyamide, cellulose acetate and hydrophilized polypropylene. Very favourable results have been obtained with an asymmetric hollow fibre of polyimide having an outer diameter of 0.85 mm.

As in the case of the known device, the device according to the invention comprises an essentially elongated housing at one end of which there is provided a closable inlet. The closing element to be used to that end is preferably made of an elastomeric material and, as is the case with the known blood collection tubes, is so constructed that it can be penetrated by the needle of an hypodermic syringe.

Partly in view of the simple construction, it is preferred that use should be made of a separator which extends in longitudinal direction of the housing.

Preferably, the separator is connected at one end to said inlet. The hollow fibres may extend in the feed channels in many different ways. A favourable embodiment comprises one or more hollow fibres which extend longitudinally within the feed channel and are closed at the end near the inlet of the housing. In that case the hollow fibres may extend practically parallel to the direction of the housing. See FIGS. 1, 2 and 5 Alternatively, one or more hollow fibres may extend helically within the feed channel about a longitudinally positioned pin. See FIG. 6 Instead of being closed at one end, the fibres may be doubled upon themselves and have their two ends connected to the area for the cell-free fraction.

For the construction of the housing and the separator various, preferably thermoplastic, materials may be employed. As examples of suitable materials may be mentioned glass, polyethylene, polypropylene, polystyrene, polyvinylidene chloride, polyamide and polyethylene terephthalate.

These materials also may be used if in the device according to the invention, as in the case of the known blood collecting tubes, a vacuum need be created and maintained for a considerable period.

The separator is essentially formed by a narrow feed channel through which the cell-containing liquid is passed over the wall of the hollow fibres. For the feed channel various shapes are conceivable both as far as the cross-section perpendicular to the liquid stream is concerned and as regards the variation in shape from the beginning to the end of the channel. The cross-section may for instance be rectangular, elliptical, square or round. Particularly when two or more hollow fibres are employed, use may be made of a channel having a multi-lobal cross-section, each lobe containing one or more fibres. For simplicity of construction it will generally be preferred to use a round cross-section. In this connection a distinction may still be made between a construction in which the cell-containing liquid passes through a hollow tube serving as a narrow feed channel and a construction in which the cell-containing liquid is passed externally of a concentric tube closed at both ends and positioned within the housing, in which tube at a short distance from the downstream end then are provided openings for admitting the cell-containing fraction. A suitable embodiment comprises hollow fibres so arranged about the tube that in the annular feed channel they run practically parallel to the axis of the tube of which the outer diameter is only a little smaller than the inner diameter of the housing. If the hollow fibres are kept in their position by means of grooves provided in a feed channel, use may with advantage be made of a construction in which the fibres are helically wound about the inner tube. The variation in shape from the beginning to the end of the channel is generally defined by the dimensions and the shape of the housing.

A favourable embodiment of an apparatus according to the invention comprises a housing, having a part with a closable inlet, an area for the cell-containing fraction and a membrane separator and a part sealed off therefrom except for the passage of the hollow fibres, in which latter part there is the area for the cell-free fraction. This bipartite housing may be composed of an integrated whole or of separate pieces. In the case where the housing is made up of two separate pieces, these may advantageously be joined by a screw and/or with a glue. Upon admitting the cell-containing liquid an excess pressure will be created which will subsequently be made use of to bring about the separation process. To this end the device is provided with a deaeration filter both in the area for the cell-containing fraction and in the area for the cell-free fraction. In the case where the cell-containing liquid is passed through the feed channel under the action of a vacuum prevailing throughout the device, the deaeration filters are left out. Preference is then given to a construction comprising a tube which is closable at one end or at two ends.

The device according to the invention is not only suitable for collecting samples of plasma, which plasma can subsequently be examined in situ. It also excellently lends itself for use in an epidemiological investigation, in which a large group of persons are to be examined for the presence or absence of contagious diseases. In that case use is made of a housing of a transparent material and the area for the cell-free fraction contains a diagnostic reagent. An advantageous embodiment comprises a diagnostic reagent on the wall of the area for the cell-free fraction.

The invention will be further described with reference to the accompanying figures. The embodiments described below are, of course, not to be construed as limiting the scope of the present invention.

FIG. 1 is a highly enlarged sectional view of a device according to the invention in longitudinal direction.

FIG. 2 is a cross-sectional view of the same device along the line II—II.

FIG. 3 is a highly enlarged section in longitudinal direction of a alternative embodiment of a device according to the invention.

FIG. 4 is a highly enlarged section in longitudinal direction of a variant embodiment comprising means for conducting a diagnostic test.

Figure 5:
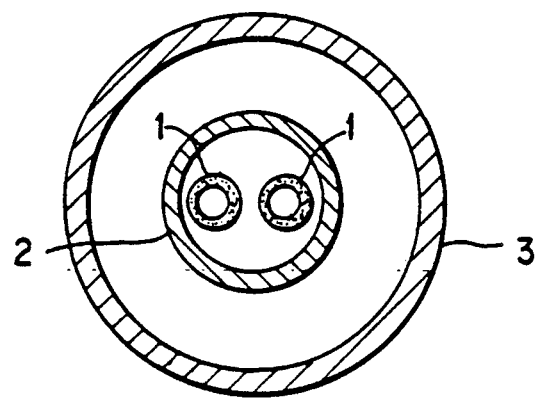
FIG. 5 is a cross sectional view of a device corresponding to the membrane separator depicted in FIG. 2 but possessing 2 hollow fibers.
Figure 6:
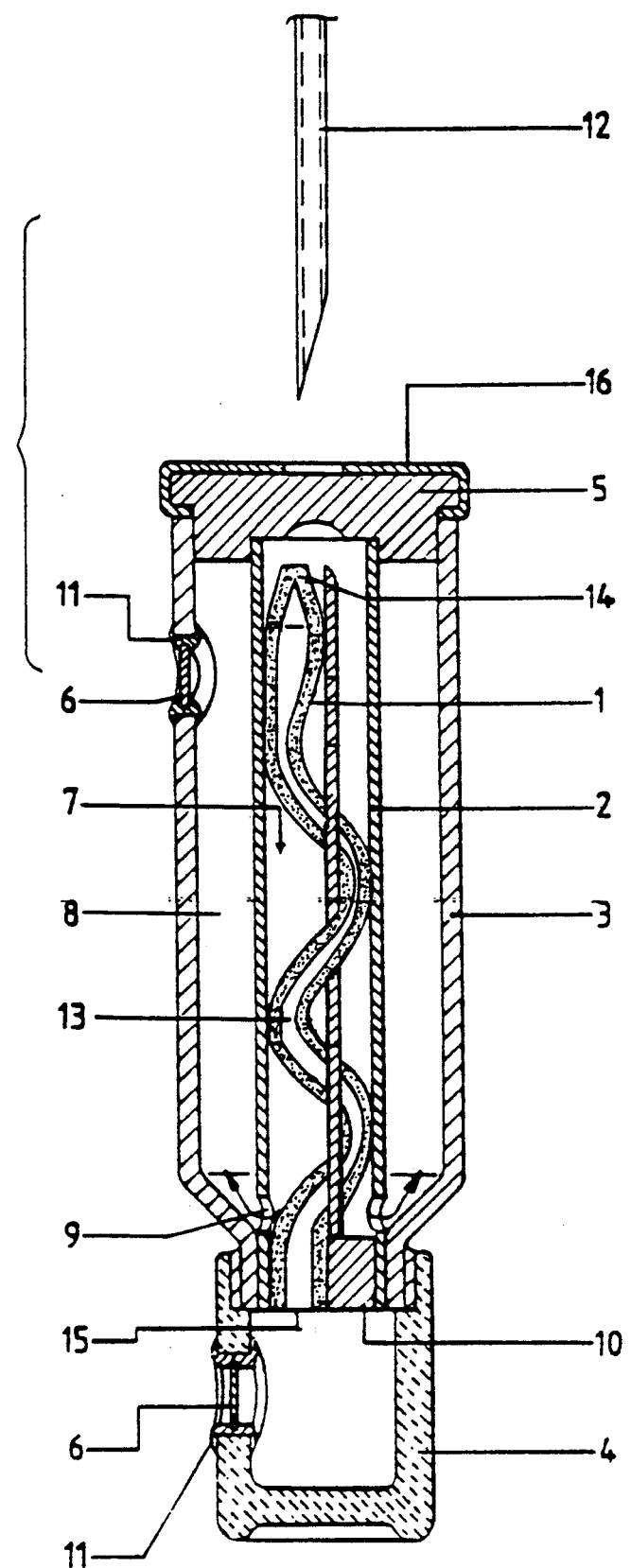
FIG. 6 is a cross sectional view of a device according to the invention in longitudinal direction, wherein a hollow fiber extends helically within a feed channel about a longitudinally positioned pin.

In FIG. 1 one part of the housing of the device is referred to by the numeral 3 and the other part with the area for collecting the cell-free fraction by the numeral 4. Inside part 3 of the housing is the separator in the form of a hollow tube 2 which contains a hollow fibre 1 which has a closed end 14. The inlet of the housing 3 is closed with a rubber cap 5 which also serves to seal the hollow tube 2. At its other end the tube 2 ends in the area 4 and is sealed off therefrom, except for the discharge opening 15 of the hollow fibre, by means of, for instance, polyurethane 10. Just above the point where the tube 2 ends in the area 4 are a number of blood outflow openings 9 through which the cell-containing fraction has access to an area 8. In both parts of the housing 3, 4 are deaeration filters 6, 11.

As appears from the cross-sectional view along the line II—II in FIG. 2, the housing 3 has a round cross-sectional area within which both the hollow tube 2 and the hollow fibre 1 are accommodated.

When the above-described device is employed in actual practice a needle 12 is used to penetrate the rubber cap through an opening in a protective plate 16, after which a cell-containing liquid 7, such as blood, is injected into the hollow tube 2 with a syringe.

The small distance between the wall of the hollow fibre 1 and the inner wall of the hollow tube 2 causes the liquid to flow in contact with the wall of the hollow fibre 1 at a high shear rate. The resulting increase in pressure relative to the pressure prevailing in a lumen 13 will cause cell-free liquid (plasma) to flow into the lumen 13 of the hollow fibre 1 and subsequently pass into the area 4.

FIGS. 3 and 4 show variant embodiments according to the invention, with a vacuum being created throughout the device.

FIG. 3 shows a provision in the form of a breaking groove 19, which makes it possible for the area 4 with the cell-free liquid (plasma) to be detached from the device. FIG. 4 shows a conceivable combination with a means for conducting a diagnostic test. The reagents for a test may be on a filter material 17 or form a layer 18 on the wall of the area 4.

The invention will be further elucidated in the following examples.

EXAMPLE I

In this example use was made of device illustrated in FIG. 3. The outside was formed by a plastic tube having a length of 8 cm and an internal diameter of 12 mm. The membrane separator fixed inside it consisted of a plastic tube having an internal diameter of 0.93 mm in which there extended a hollow, polyether imide fibre closed at one end and having an external diameter of 0.82 mm and a length of 6 cm. In the device a vacuum prevailed. Through the closable inlet 4 ml of bovine blood were introduced into the device and in a relatively short time 0.48 ml of plasma were obtained. During this filtration no hemolysis was observed. When the test was repeated with the same fibre in a plastic tube having an internal diameter of 1.16 mm, 0.03 ml of plasma were obtained.

EXAMPLE II

The construction of the device used in this example was analogous to that of the device in Example 1, except that the plastic tube having a length of 8 cm and a diameter of 12 mm contained three membrane separators positioned parallel to each other. Each membrane separator consisted of a plastic tube having an internal diameter of 0.93 mm in which there extended a hollow, polyether imide fibre closed at one end and having an external diameter of 0.82 mm and a length of 6 cm. By filtration of 4 ml of pig's blood 0.65 ml of plasma were obtained in a short time.

I claim:

1. A device for separating a cellcontaining liquid into a cell-containing fraction and a cell-free fraction, which device comprises an essentially elongated housing at one end of which there is provided a closable inlet, which housing contains a first area for receiving the cell-containing fraction, a second area located adjacent an opposite sealed end of said housing for receiving the cell-free fraction, and a membrane separator, which membrane separator comprises an enclosed narrow feed channel which is at one end in flow communication with the closable inlet for introduction of the cell-containing liquid and at the other end with the first area for receiving the cell-containing fraction which lies between said enclosed narrow feed channel and said housing, said membrane separator contains one or more hollow fibers which pass through said sealed end of the housing and at their open ends are in flow communication with the second area for receiving the cell-free fraction.

2. A device according to claim 1, wherein said one or more hollow fibers extend helically within the membrane separator about a longitudinally positioned pin.

3. A device according to claim 1, wherein both in the first area for the cell-containing fraction and in the second area for receiving the cell-free fraction there is provided a deaeration filter.

4. A device according to claim 1, wherein the housing is of a transparent material and the second area for receiving the cell-free fraction contains a diagnostic reagent.

5. A device according to claim 4, wherein the diagnostic reagent is on the wall of the second area for receiving the cell-free fraction.

* * * * *

UNITED STATES PATENT AND TRADEMARK OFFICE
CERTIFICATE OF CORRECTION

PATENT NO. : 4,995,967
DATED : February 26, 1991
INVENTOR(S) : VAN DRIESSCHE It is certified that error appears in the above-identified patent and that said Letters Patent is hereby corrected as shown below:

Col. 1, line 65, change "cellcontaining" to --cell-containing--.

IN THE CLAIMS:

Claim 1, line 1 (col. 5, line 22), change "cellcontaining" to --cell-containing--.

Signed and Sealed this

Twenty-third Day of June, 1992

Attest:

DOUGLAS B. COMER

Attesting Officer  Acting Commissioner of Patents and Trademarks